US009410113B2

(12) United States Patent
Vilendrer et al.

(10) Patent No.: US 9,410,113 B2
(45) Date of Patent: Aug. 9, 2016

(54) BIOREACTOR SYSTEM FOR THREE-DIMENSIONAL TISSUE STIMULATOR

(75) Inventors: Kent S. Vilendrer, Eden Prairie, MN (US); Blaise D. Porter, Minneapolis, MN (US); Philippe Levesque, Bloomington, MN (US)

(73) Assignee: ST3 Development Corporation, Eden Prairie, MN (US)

( * ) Notice: Subject to any disclaimer, the term of this patent is extended or adjusted under 35 U.S.C. 154(b) by 1253 days.

(21) Appl. No.: 12/258,048

(22) Filed: Oct. 24, 2008

(65) Prior Publication Data

US 2009/0111180 A1 Apr. 30, 2009

Related U.S. Application Data

(60) Provisional application No. 61/000,485, filed on Oct. 26, 2007.

(51) Int. Cl.
| | |
|---|---|
| *C12M 3/00* | (2006.01) |
| *C12M 1/00* | (2006.01) |
| *C12M 1/42* | (2006.01) |
| *C12M 1/34* | (2006.01) |
| *C12N 5/00* | (2006.01) |

(52) U.S. Cl.
CPC .............. *C12M 21/08* (2013.01); *C12M 29/14* (2013.01); *C12M 35/04* (2013.01); *C12M 41/40* (2013.01); *C12N 5/0062* (2013.01)

(58) Field of Classification Search
CPC ...... C12M 21/08; C12M 29/14; C12M 35/04; C12M 41/40; C12N 5/0062

USPC .......... 435/286.6, 289.1, 297.1, 303.1, 305.2, 435/395

See application file for complete search history.

(56) References Cited

U.S. PATENT DOCUMENTS

| | | | |
|---|---|---|---|
| 3,651,607 A | 3/1972 | Lee, II | |
| 4,130,120 A | 12/1978 | Kohler, Jr. | |
| 4,839,280 A * | 6/1989 | Banes | 435/305.2 |
| 5,330,908 A | 7/1994 | Spaulding | |
| 5,437,998 A | 8/1995 | Schwarz et al. | |
| 5,460,968 A | 10/1995 | Yoshida et al. | |
| 5,665,594 A | 9/1997 | Schwarz et al. | |
| 5,670,708 A | 9/1997 | Vilendrer | |
| 5,792,603 A | 8/1998 | Dunkelman et al. | |
| 5,795,773 A * | 8/1998 | Read et al. | 435/287.5 |
| 5,843,766 A | 12/1998 | Applegate et al. | |

(Continued)

FOREIGN PATENT DOCUMENTS

DE EP 1 186 653 3/2002

*Primary Examiner* — Michael Hobbs
(74) *Attorney, Agent, or Firm* — Dietz Law Office LLC (57) ABSTRACT

A bioreactor system for growing and conditioning tissue for research and implantation in a human or animal body is disclosed which includes one or more tissue growth chambers for growing and conditioning tissue, each chamber being defined by a housing and providing a fluid culture media cavity which can act as a reservoir. A construct for growing three-dimensional tissues is housed in each tissue growth chamber. Each chamber is connected to a source of pressurized air for applying a controlled pressure to the chamber media cavity. The tissue growth chambers can be mounted on an agitation device such as a shaker system which enhances mass transport within the chamber media cavity. A control system is provided to control the pressure and temperature of the pressurized gas delivered to the chamber media cavity and subsequently to the tissue construct.

31 Claims, 7 Drawing Sheets

(56) References Cited

U.S. PATENT DOCUMENTS

| | | |
|---|---|---|
| 5,846,828 A | 12/1998 | Peterson et al. |
| 5,902,937 A | 5/1999 | Amrani et al. |
| 6,001,643 A | 12/1999 | Spaulding |
| 6,008,049 A | 12/1999 | Naughton et al. |
| 6,060,306 A | 5/2000 | Flatt et al. |
| 6,121,042 A | 9/2000 | Peterson et al. |
| 6,171,812 B1 | 1/2001 | Smith et al. |
| 6,210,957 B1 | 4/2001 | Carpentier et al. |
| 6,432,713 B2 | 8/2002 | Takagi et al. |
| 6,599,734 B2 | 7/2003 | Takagi et al. |
| 6,607,917 B2 | 8/2003 | Takagi et al. |
| 6,794,184 B1 | 9/2004 | Mohr et al. |
| 6,855,542 B2 | 2/2005 | DiMilla et al. |
| 6,921,662 B2 | 7/2005 | Takagi et al. |
| 6,979,308 B1 | 12/2005 | MacDonald et al. |
| 7,144,726 B2 | 12/2006 | Takagi et al. |
| 7,179,287 B2 | 2/2007 | Wolfinbarger, Jr. |
| 7,270,472 B2 | 9/2007 | Carreras |
| 7,348,175 B2 | 3/2008 | Vilendrer et al. |
| 7,348,176 B2 | 3/2008 | DiMilla et al. |
| 7,410,792 B2 | 8/2008 | Vilendrer |
| 7,416,884 B2 | 8/2008 | Gemmiti et al. |
| 7,456,019 B2 | 11/2008 | Goodwin et al. |
| 7,472,604 B2 | 1/2009 | Moore, Jr. et al. |
| 7,585,323 B2 | 9/2009 | Masini et al. |
| 7,587,949 B2 | 9/2009 | Dingmann et al. |
| 7,624,648 B2 | 12/2009 | Nickel et al. |
| 7,694,593 B2 | 4/2010 | Owens et al. |
| 2003/0143727 A1* | 7/2003 | Chang ............... 435/289.1 |
| 2004/0219659 A1* | 11/2004 | Altman et al. ........... 435/284.1 |
| 2005/0002910 A1* | 1/2005 | Wolfinbarger et al. ...... 424/93.7 |
| 2005/0101008 A1 | 5/2005 | Diresta et al. |
| 2006/0199260 A1 | 9/2006 | Zhang et al. |
| 2009/0215104 A1 | 8/2009 | Taboas et al. |

\* cited by examiner

BIOREACTOR SYSTEM FOR THREE-DIMENSIONAL TISSUE STIMULATOR

CROSS-REFERENCED TO RELATED APPLICATIONS

This application is a non-provisional application of Application No. 61/000,485, filed Oct. 26, 2007 and claims priority from that application which is also deemed incorporated by reference in its entirety in this application.

STATEMENT REGARDING FEDERALLY SPONSORED RESEARCH OR DEVELOPMENT

Not applicable

BACKGROUND OF THE INVENTION

I. Field of the Invention

The present invention relates to a method and apparatus for growing and conditioning tissue engineered medical products and in particular to a method and apparatus for a servocontrolled bioreactor with a dynamic pressurization system and a chamber with an integrated nutrient reservoir for conditioning tissue engineered medical products (TEMPs) in the orthopedic, secretory organ and vascular areas. TEMPs can include, without limitation, various types of tissue in several areas. Within the orthopedic area TEMPS can include: cartilage, bone, meniscus, ligaments, tendons, muscle, and other musculo-skeletal devices. Within the secretory organ area TEMPs can include liver, kidney, skin and other organs. Within the vascular area TEMPs can include, but are not limited to, heart valves, blood vessels, and cardiac patches. Other TEMPs can include: cornea, bladder, urethra, small intestine or any other tissue that might be replaced in the body.

Tissue engineering is a rapidly growing area that seeks to create, repair and/or replace tissues and organs by using combinations of cells, biomaterials, and/or biologically active molecules. It is an interdisciplinary field that integrates aspects of engineering, and other quantitative sciences, with biology and medicine. Research and technology development in tissue engineering promises to revolutionize current methods of health care treatment and significantly improve the quality of life for millions of patients. As one indication of the scope of the problem that tissue engineering addresses, worldwide organ replacement therapies utilizing standard organo-metallic devices consume 8 percent of medical spending, or approximately $350 billion per year. Organ transplantation is another option for replacing damaged or diseased tissue, but one that is severely limited by donor availability. Tissue-engineered products hold the promise for true functional replacement. However, despite early laboratory successes, few functional tissue engineered products are currently available for clinical use.

Researchers have sought to develop living alternatives to traditional "man-made" medical devices. These TEMPs use the patient's own cells to create replacement devices that can be cultured and grown once they are implanted. Through design and fabrication of biomaterials and specification of cells or biomolecules, it is hoped that TEMPs will play a major role in many future regenerative medicine therapies. In the orthopedic area considerable energy is being expended on the development of tissue engineered cartilage, meniscus, bone, ligaments or tendon replacements. Likewise, similar efforts are being made to develop new replacements for heart valves, arteries, heart muscle tissue and venous valves. Tissue engineered replacements for secretory organs such as the liver, kidney and skin also hold great promise for future therapies. Tissue engineered skin replacements are already available and are dramatically improving the outcomes for patients with diabetic ulcers, as well as burn victims and those undergoing certain cosmetic therapies.

The field of tissue engineering in recent years has included the development of bioreactors which provide a means of conditioning a developing tissue by applying mechanical stresses to a construct (cells or cell seeded substrate while circulating nutrient media around and or through the construct. Cells and tissues grown in bioreactors able to mimic physiological conditions including mechanical forces have enhanced tissue development, mechanical properties and function. These bioreactor systems typically include a bioreactor chamber coupled to a device which generates motion and applies forces, pressures and or deformations to the tissue construct via a mechanical feed-through (push or pull rod). Additionally, these systems typically include a separate reservoir that contains a nutrient media for sustaining the cells within the tissue construct. The reservoir is often connected to the bioreactor chamber via tubing and a mechanical pumping system. The biochemistry of the nutrient media can be maintained by exposing it to the environment that is created within an incubator system. The incubator maintains the temperature, as well as gas concentrations ($CO_2$, $O_2$, etc.). The exposure of the media to the environment is often accomplished by placing a vented reservoir directly in the incubator or by circulating the media through gas permeable tubing located inside the incubator. Gas concentrations can also be bubbled through the media to maintain appropriate culture conditions.

II. Related Art

Other bioreactor systems have addressed aspects of the need for an apparatus dedicated to growing and conditioning tissue engineered medical products. As will become apparent, the present device described in this patent application surpasses those systems in several respects.

Spaulding et al. (U.S. Pat. No. 5,330,908), (U.S. Pat. No. 6,001,643) and Schwartz (U.S. Pat. No. 5,437,998), (U.S. Pat. No. 5,665,594) disclose bioreactor systems that operate at ambient pressure and in which mechanical stresses to the cells are applied by rolling the chamber about its cylindrical axis. Conversely, the bioreactor system of the present invention applies a static or varying pressure to the chamber and subsequently the tissue construct within while the chamber is agitated via a multi-axis motion device.

Dunkleman et al. (U.S. Pat. No. 5,792,603), Peterson et al (U.S. Pat. No. 5,846,828) and Vilendrer et al (U.S. Pat. No. 7,348,175) disclose bioreactor systems for vascular grafts in which an alternating or varying flow or backpressure from an external media storage device is provided via a tube and pumping system. Control of the flow and/or back pressure is provided by an external flow pump. Whereas, in the present system, the sealed chamber and media reservoir are combined thus eliminating the need for an interconnecting tube to create flow. Additionally, pressurization in the present system may be provided directly via a high pressure air source and servovalve controlled by a microprocessor servocontrol system which supplies specific air pressures to one side of a deformable membrane. As the membrane deforms the pressure is transferred to the interior of the chamber. Applegate et al. (U.S. Pat. No. 5,843,766) discloses a bioreactor system for grafts with inlet and outlet ports for evenly distributing media flow across and generally parallel to the tissue substrate that also requires a separate external nutrient fluid reservoir. In the present system, the agitation of the chamber and deformation of the membrane aid in convective mass transport.

Amrani et al. (U.S. Pat. No. 5,902,937) discloses an in vitro testing system for testing blood/tissue interaction that utilizes twin chambers with top and bottom tissue membranes and an internal conduit for conducting blood between the chambers. Blood flow actuation is provided by pistons that alternately depress the membranes on each chamber to displace blood from one chamber to the other. Naughton et al. (U.S. Pat. No. 6,008,049) discloses a diffusion gradient bioreactor system for conditioning tissue engineered liver whereby the tissue is exposed to two nutrient flows. The primary purpose of their device is to move solutes through the device via flow. With the present system only one sealed chamber is needed and it is not interconnected with another chamber to create flow. Also, as indicated above, pressurization in the present invention may be provided directly through a deformable membrane. The high pressure air source is controlled via a microprocessor-controlled servovalve.

Flatt et al (U.S. Pat. No. 6,060,306) discloses a bioreactor chamber with a substrate that is sealed to the sides of the chamber. Using various mechanical actuation means, a pressure differential is created across the substrate to create a fluid flow through it. In the present system, the substrate is not sealed to the sides of the chamber so any applied pressure does not create a differential across the substrate to create a fluid flow through it.

Peterson et al (U.S. Pat. No. 6,121,042) and Carpentier et al (U.S. Pat. No. 6,210,957 B1) disclose bioreactor systems that provide flow about a substrate that is attached to a structure. These systems pump fluid through the chamber using inlet and outlet ports, or actuate the structure to control media flow characteristics around the substrate. In contrast, the substrate of the present system is not attached to a structure but is free to move within the chamber nor is fluid pumped through the chamber to create controlled media flow characteristics. Mechanical agitation of the chamber to enhance fluid mass transport is provided via the shaking motion of a mechanical shaking system and a hydrostatic stress may be provided by pressurization of the membrane as indicated above.

Smith et al (U.S. Pat. No. 6,171,812 B1) and Vilendrer (U.S. Pat. No. 7,410,792 B2) further disclose a bioreactor system that has means for perfusion and application of forces to the substrate within the bioreactor chamber. In the present system, neither of these forces within the chamber is explicitly provided.

Takagi et al (U.S. Pat. No. 6,432,713 B2), (U.S. Pat. No. 6,599,734 B2), (U.S. Pat. No. 6,607,917 B2), (U.S. Pat. No. 6,921,662 B2) describes bioreactor systems which utilize a sealed chamber that is interconnected to a medium reservoir via a tube or circuit. Pressurization of the chambers is provided via actuator driven pistons and control of the system is accomplished using regulators and timers or a microcomputer that turns various valves on at the appropriate times. Tagaki et al (U.S. Pat. No. 7,144,726) also describes a bioreactor chamber with fluid port and a magnetically driven pressing plate for creating pressurization within the chamber. These references do not suggest the use of a sealed combined chamber.

While some of the above described systems have worked in certain applications, there remains a need in the art to simplify the method and apparatus for growing and conditioning tissue while maintaining environmental control.

SUMMARY OF THE INVENTION

The present invention addresses a need in the art for a method and apparatus for growing and conditioning tissue and other needs which will be appreciated by those skilled in the art upon reading and understanding the teachings of the present invention.

The subject matter of the present development relates to a bioreactor system for growing and conditioning tissue in various embodiments including a bioreactor system for three-dimensional tissue growth and stimulation. This system features a bioreactor tissue growth chamber capable of dynamic pressurization and an integrated fluid culture media reservoir which does not require a flow loop. In accordance with the present invention, it has been discovered that beneficial mechanical stress can be applied directly to a construct by deforming a membrane on one or more surfaces of the tissue growth chamber without the need for mechanical feedthroughs. Additionally, integrating the reservoir within the bioreactor chamber can eliminate the culture media flow loop and associated tubing. Consequently, the present invention features a bioreactor or tissue growth chamber that couples the stress application with the nutrient media exchange mechanism in one unit.

One embodiment includes a bioreactor system for growing and conditioning tissue for research or future implantation in a patient. The system includes one or more tissue growth chambers for growing and conditioning the tissue and each tissue growth chamber includes a housing which is a fluid culture media reservoir for growing and conditioning at least one tissue construct that may include one or more substrates for growing three-dimensional tissues. The tissue growth chamber includes separate ports for introducing pressurized air or other gas and fluid culture media. The bioreactor system further includes at least one pressurized gas space proximal to or contained within the chamber and a control system to selectively control the pressure and temperature of the gas (normally air) from the source of pressurized gas which is transmitted to the tissue growth chamber via a non gas-permeable membrane to create a dynamic hydrostatic state of stress to developing tissues or cells. In this manner, a programmable static or dynamic pressure profile can be delivered. A substrate on which the three-dimensional tissue construct may be grown may include bio-compatible three-dimensional framework having interstitial spaces bridgeable by cells. The one or more tissue growth chambers may be mounted on a shaker to agitate the culture media to enhance convective mass transport. At least one device for facilitating gas exchange within the chamber is provided to maintain the appropriate gas concentration (atmosphere). This may be a gas-permeable membrane between the chamber and a desired gas environment.

The embodiment may include a system for distributing pressurized air and mechanically agitating tissue growth chambers which are designed to be contained in an incubator and interface with a computer-controlled system and a source of dried, heated air, normally external to the incubator.

DETAILED DESCRIPTION

In the following detailed description, reference is made to the accompanying drawings which form a part hereof, and in which is shown by way of illustration specific embodiments in which the invention may be practiced. The embodiments shown and described are meant as examples only and are not intended to limit the scope of the concepts of the invention in any manner. Illustrative embodiments are described in sufficient detail to show a full grasp of the invention by the inventors and to enable those skilled in the art to practice the invention. It will be understood that the embodiments may be combined, or that other embodiments may be utilized and that structural, logical and electrical changes may be made without departing from the spirit and scope of the present invention. The following detailed description provides examples, the scope of the present invention being defined by the appended claims and their equivalents.

Figure 1A:
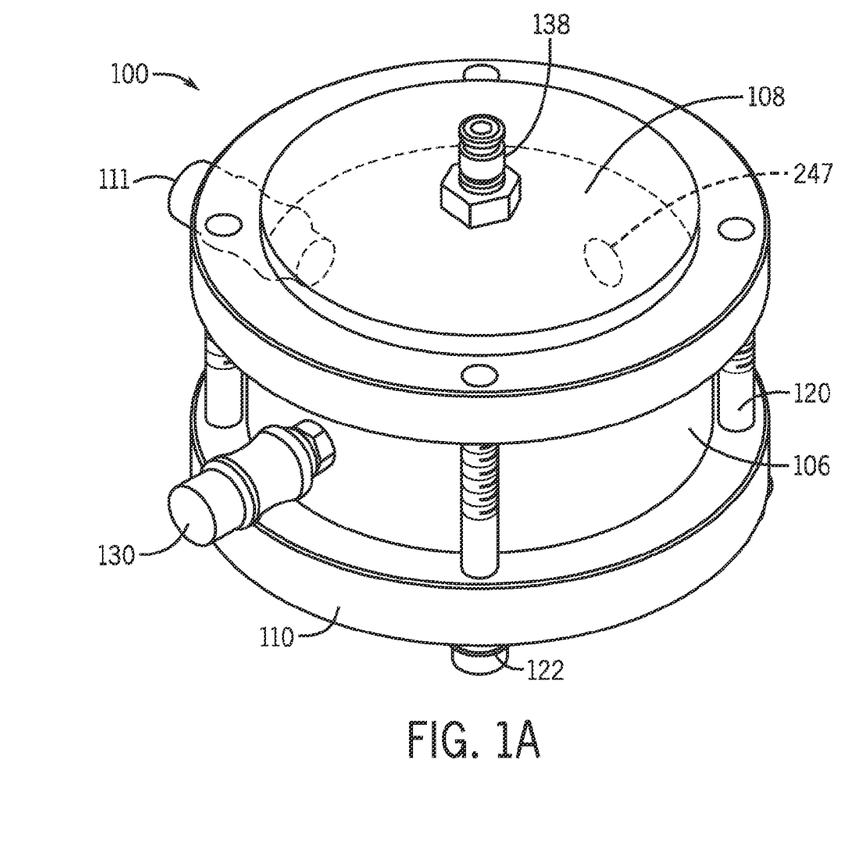
FIG. 1A shows a bioreactor chamber according to one embodiment of the present invention.
Figure 1B:
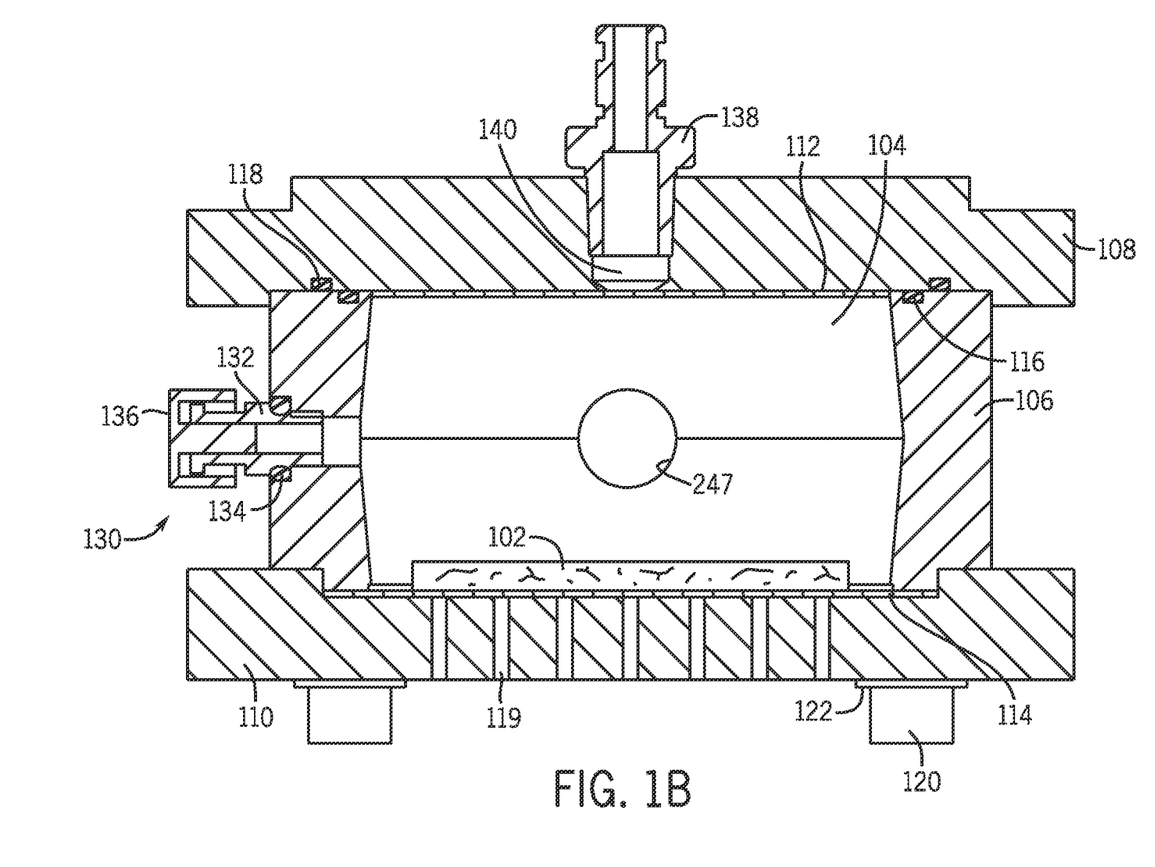
FIG. 1B is a cross-sectional view of the bioreactor chamber shown in FIG. 1A.

The present disclosure relates to a method and apparatus for a bioreactor system for three-dimensional tissue stimulation featuring dynamic pressurization and an integrated reservoir which does not require a flow loop. This will be described with reference to FIGS. 1A, 1B, 2, 3 and 4. FIG. 1A shows a bioreactor or tissue growth chamber, generally at 100 and FIG. 1B depicts a cross-sectional view of the tissue growth chamber 100 of FIG. 1A. One or more of these chambers may be used with the tissue growing and conditioning system of the invention. In one current embodiment, for example, up to 12 chambers can be included.

As seen in FIG. 1B, a tissue construct 102 has been created and placed into a main hollow chamber or media cavity 104 defined by a main housing 106 which is closed by upper and lower endcaps 108 and 110, respectively. The term "construct" may refer to the tissue itself or a tissue/substrate combination. The chamber media cavity 104 is further sealed on both upper and lower ends with membranes as at 112, 114, respectively. In this embodiment, membrane 112 is a non gas-permeable material and membrane 114 is gas-permeable and communicates with vent holes for gas exchange shown at 119 to facilitate gas exchange between the chamber media cavity 104 and a desired external gas environment. Other chamber embodiments may include different membrane configurations utilizing as few membranes as none or as many as necessary to achieve the desired media cavity pressurization and or media gas concentration.

The tissue construct is housed in the tissue growth chamber but is not attached to the chamber. The substrate may be permeable and the culture media can circulate through the substrate to contact all surfaces of the construct. The substrate may be fabricated from a material designed to facilitate three dimensional tissue growth and include a biocompatible three dimensional framework 103 that includes interstitial spaces 105 that are bridgeable by cells (not shown). That substrate material may be biological in nature and be comprised of extracellular matrix, decellularized tissue, native tissue explants, polymer matrices, woven fiber meshes, porous ceramic lattices, porous metal structures, or any other type of material that supports cell growth and differentiation. The tissue construct may also be substrate free, and be comprised of cells alone. The tissue construct is three dimensional in nature and may be tissue-engineered cartilage, skin, bone, liver, lung or some other tissue-engineered graft or medical device. It will be appreciated that the tissue can be grown without using a substrate as by using a cell suspension or aggregate of cells.

The tissue growth chamber membranes may be either gas permeable or non gas permeable and are made out of a material that permits elastic deformation. The membranes may either be flat or curved or fabricated with a specific geometry to cover and seal the media cavity appropriately. The membranes 112, 114 are held in place by a pair of opposed endcaps/support structures at 108, 110, respectively, that sandwich/clamp the membranes between the endcaps and the main housing sidewall 106. Optionally, and particularly, if the upper membrane is relatively stiff, spaced opposed o-ring members as at 116 and 118 or some other equivalent sealing mechanism, such as glue, soft deformable sealant, tape, caulk, silicone grease, or the like, may be used to seal the membrane 112 between the chamber main housing sidewall 106 and the endcap 108. The membranes 112, 114 may also be fixed, bonded, or a permanent component of either the endcaps 108,110 or the chamber main housing sidewall 106. Sealing mechanisms may also be provided for the membrane 114 between housing sidewall 106 and endcap 110.

The endcaps themselves are held in place by the compressive action of a plurality of fasteners that may be bolts 120 (FIG. 1A) that are threaded through washers 122 and endcap 110 and are threaded into corresponding openings in opposite endcap 108 at 124. It will be appreciated that the bolts may be replaced by other suitable fastening elements such as, for example, threaded tie rods provided with nuts on either end. Alternatively, the endcaps 108, 110 may also be held and sealed against the membranes 112, 114 and chamber main housing sidewall 106 via threaded connections or some other clamping means.

Access is provided to the chamber after it has been sealed, such that media may be deposited/injected into the chamber media cavity 104 via a media port 130 (inlet/outlet access port) which includes an access opening into the chamber media cavity 104. The media port 130 includes a media fitting 132, o-ring seal 134 and plug fitting 136.

The o-ring seal 134 in some embodiments may be replaced by any of several other sealing techniques and devices including Teflon® (polytetrafluoroethylene) tape, silicone grease, interference thread fit, glue, epoxy, caulk, or any other satisfactory sealing mechanism. The media port may also be machined, molded or directly fabricated as an integral part of the chamber main housing. Depending on the application, the chamber may be constructed without an access port or provided with as many media ports as is required for injecting media and bleeding out air. For some applications, it may be desirable for air to remain in the chamber. Once the chamber cavity 104 is filled or partially filled with media, the media fitting 132 is closed as with plug fitting 136. An optional additional port 138 may be provided in the chamber main housing to accommodate a pressure transducer to verify and monitor the internal chamber pressure.

The application of a hydrostatic state of stress is an important aspect of the operation of the bioreactive chamber. Accordingly, a pressurized gas fitting 138 is provided to supply controlled pressurized gas (or air) into a pressurized gas space 140 in endcap 108. In the embodiment of FIGS. 1A and 1B, the pressurized gas fitting 138 is a quick-disconnect fitting, but any type of fitting that allows the user to connect a pressurized air/gas supply to the chamber could be used. The pressurized gas space is open to membrane 112 such that a change in gas pressure in space 140 causes Membrane A 112 to deform and increase the pressure in the chamber media cavity 104.

In the illustrative embodiment, membrane 112 is non-permeable and membrane 114 is permeable. Therefore, gas exchange can occur through membrane 114 and vent holes 142 provided in endcap 110. Of course, in the event that no gas exchange is required, as is the case in certain applications, both membranes could be non gas-permeable. In certain other applications, the addition of pressurized gas directly to the inside of the chamber may be desired and, in such embodiments, membrane 112 is selected from gas permeable materials and membrane 114 is of a non gas-permeable material. In that arrangement, the pressurized gas may contain the appropriate concentrations of gas species needed for successful cell culture.

Figure 2:
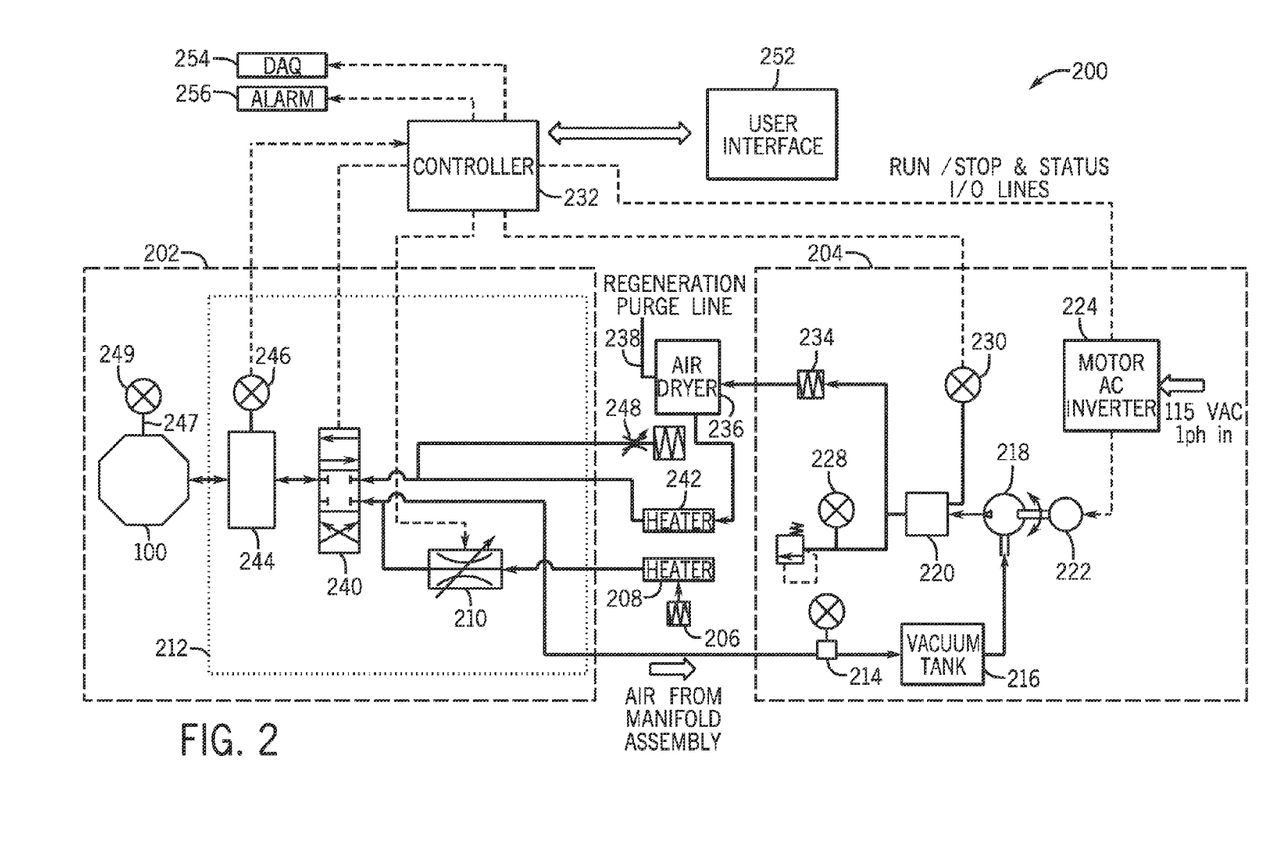
FIG. 2 shows a schematic functional diagram of a microprocessor servocontrolled bioreactor system according to one embodiment of the present invention.

FIG. 2 shows an embodiment of a dynamic pressurization and control system, generally 200, suitable to be used to create a dynamic hydrostatic stress state in the chamber 104 of FIGS. 1A and 1B for the tissue construct 102. The pressurization system, as will be described below, includes a Pressure Pack shown in dashed lines at 204 for creating a pressurized supply of air or other system gas which may be generally in the 80-150 psig range and to provide a vacuum in the 5 psia range, however, any pressure and vacuum range that would be required is acceptable.

Air to be pressurized starts out as ambient air that is drawn into the system through a filter 206 and then warmed by an associated heater 208, which may be a tubular air heater as in the illustrative embodiment. The warmed air travels to a proportional valve 210 attached to a manifold assembly indicated by a dotted line at 212 located inside the incubator 202. The proportional valve 210 controls the amount of air that is drawn past a vacuum gauge 214 into a vacuum tank 216, through a compressor 218 and into a pressure tank 220. The compressor 218, in turn, is coupled to an AC motor 222 which is controlled by an AC motor inverter drive 224 which controls the motor at a constant rpm.

Pressure tank 220 is used as an accumulator for storing pressurized air supplied by compressor 218. A pressure relief valve is provided at 226 with integrated pressure gauge 228. The pressure relief valve may be set to any desired pressure and is normally set to about 100 psig (or any other appropriate pressure limit) as a safeguard to prevent over pressurizing the system. A pressure transducer 230 is connected to the pressure tank and to a controller 232 which is also connected to control proportional valve 210 to complete a feedback loop with control software to maintain a desired pressure in the tank 220. In this manner, if the pressure in the tank 220 falls below the desired pressure level, the controller 232 sends a signal to proportional valve 210 to open incrementally to increase air flow to the compressor and thereby increase the tank pressure. Conversely, if the pressure in the tank is above the desired pressure level, the controller signals the proportional valve to begin to close, which decreases the available air that can be compressed and the air pressure in the tank decreases.

Prior to being supplied to the incubator bioreactor chamber, the pressurized air is passed through a filter 234 (or series of filters) to remove any particles and then through an air dryer 236 to prevent moisture from accumulating in the line. Moisture is expelled out of the dryer into the ambient air via a purge line 238.

Upon entering the incubator, the pressurized air travels through the manifold assembly 212. A three-way ported servovalve 240 when commanded in one direction ports the pressurized air supply to a gas distribution manifold 244 which, in turn, subsequently supplies pressurized air to the chambers 100. Pre-drying the air reduces the potential for corrosion of the servovalve 240. Prior to encountering the servovalve 240, the air is passed through an air heater 242 wherein it is heated to match the temperature inside the incubator. A pressure transducer 246 on gas distribution manifold 244 monitors the pressure inside the manifold 244. If the servovalve 240 is in a completely closed position and the air supply to the gas distribution manifold 244 is blocked, as shown in FIG. 2, the air slowly escapes out of a bleed valve 248. The servovalve 240 is controlled via an electric voltage signal output from the system controller 232. The system controller 232 monitors the pressure in bioreactor chambers 100 via pressure transducer 246 or optional pressure transducer 249 through port 247 in chamber 100 and sends a control signal to the servovalve 240 to maintain the desired pressure waveform. Additionally, the controller 232 can be used to monitor the pressure output signal of an optional pressure transducer 250 which is connected directly to a chamber 100 and can be used for calibration purposes to correlate the pressure in chamber 100 with the pressure in the gas distribution manifold 244. Optional pressure transducer 249 can also be used as an alternate feedback device to control the servovalve 240 mounted on the gas distribution manifold 244.

When the servovalve 240 is commanded to provide pressure, high pressure gas enters the gas distribution manifold 244 and pressurizes the chambers 100. When the servovalve is commanded to reduce pressure, it connects manifold 244 with the vacuum tank 216 as needed to reduce the chamber pressures to a lower value. The pressure command can take any of many forms to control the pressure supplied to the manifold on a steady or time-variable basis including a static setting, a sinusoidal, trapezoid, ramp or physiologic waveform. A personal computer 252 provides a user interface for communicating with the controller 232. Additionally, controller 232 can be configured to communicate conditions within the bioreactor system to the outside world as via a data acquisition system (DAQ) 254 and alarm 256. Advantageously, in this manner, using a non gas-permeable membrane 112, the pressurized air supply can be kept separate from the gas mixture inside the incubator, yet produce the desired hydrostatic pressure effect on growing tissue.

It will also be appreciated that the configuration of FIG. 2 could also be constructed with all (or some combination of) the components of the manifold assembly located outside the incubator. In embodiments for certain applications, it is acceptable for the air from the incubator to mix with the pressurized air supply. In such embodiments, inlet filter 206 and bleed-valve/silencer 248 can be moved inside the incubator 202 and the inlet air would not need to be heated between the filter 206 and the proportional valve 210.

Figure 3:
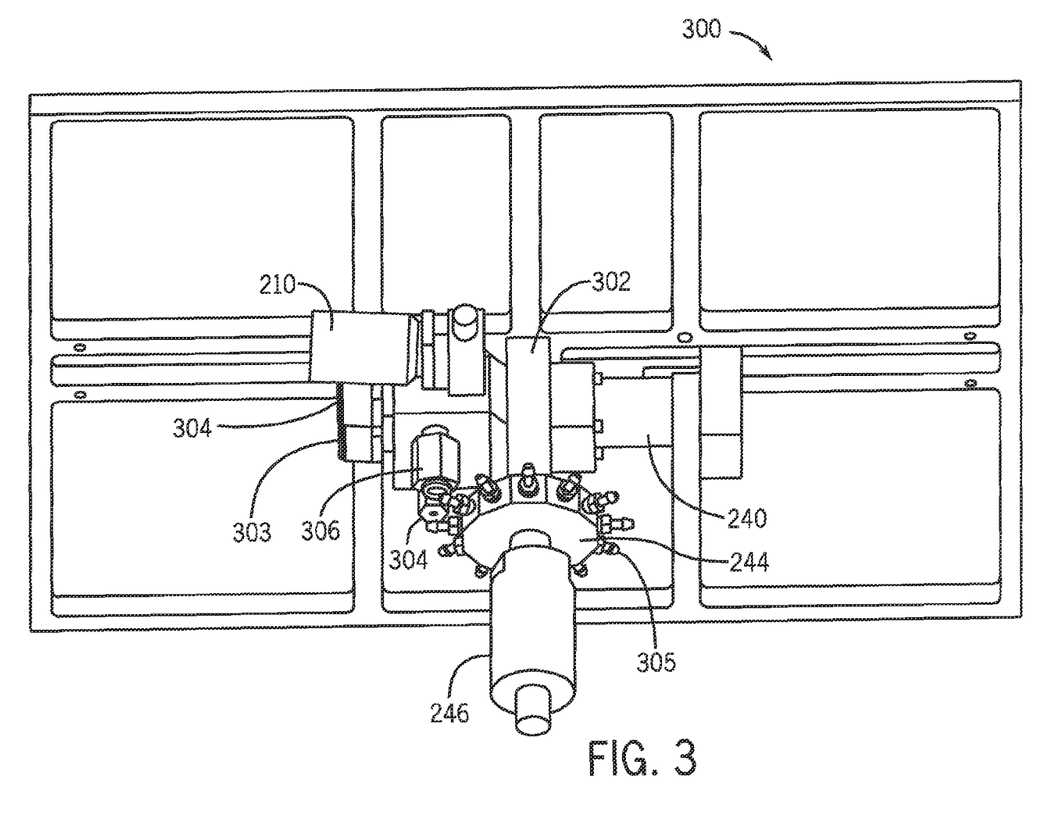
FIG. 3 illustrates one embodiment of a pressure manifold assembly shown schematically in FIG. 2 including various components that are mounted to the manifold.

FIG. 3 illustrates one embodiment of a pressure manifold assembly including gas manifold components shown schematically in FIG. 2. The manifold assembly is mounted on an incubator shelf 300 designed to slide into a standard incubator shelf holder (not shown). High pressure air from the pressure pack is received in a servovalve manifold 302 through a high pressure inlet fitting 303 and is routed through servovalve 240 where it is either diverted to a high pressure outlet 304, or directed to the gas distribution manifold 244. In the manifold, pressure is set to the desired dynamic pressure using feedback from the pressure transducer 246 which is connected to the center of the gas distribution manifold 244. The pressurized air/gas exiting the manifold is supplied to a plurality of tissue growth chambers 100 through a plurality of manifold distribution fittings 305 which may be connected by non gas-permeable chemically inert tubing (not shown) to each chamber.

As indicated, the pressure in the chambers 100 may be reduced as needed by commanding the servovalve 240 to connect to the vacuum tank 216 which rapidly reduces the air/gas pressure until the appropriate pressure has been reached. Air/gas exits the servovalve by traveling through a vacuum outlet fitting 305 connected to vacuum tank 216.

It will be recognized that in a different embodiment, an additional air supply may be required to maintain an appropriate pressure, therefore a secondary air inlet (in addition to the proportional valve inlet 210) may be necessary. Accordingly, the servovalve manifold 302 in FIG. 3 includes a secondary vacuum inlet that has been shown sealed with a plug at 306, which can be used if larger airflow is necessary.

Figure 4A:
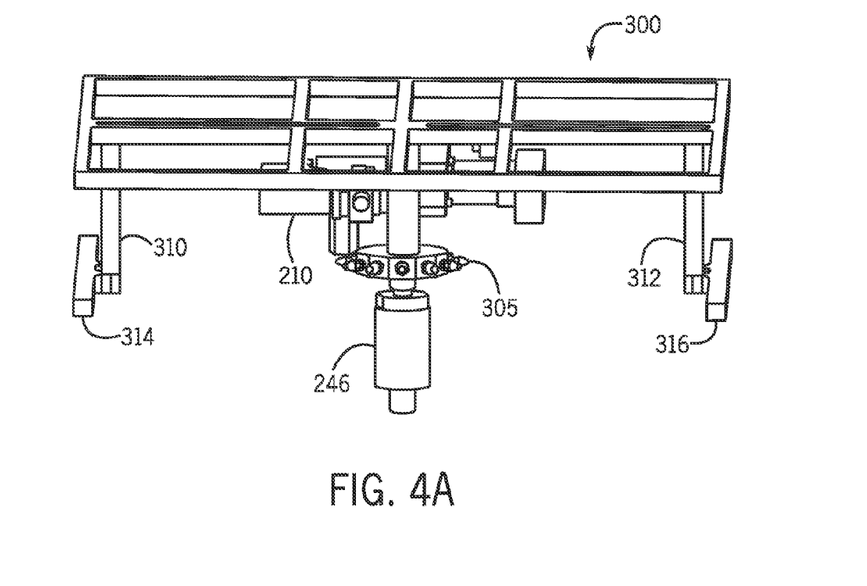
FIGS. 4A and 4B depict assemblies that fit within the incubator according to one embodiment of the present invention, FIG. 4A showing a manifold assembly and FIG. 4B showing bioreactor chambers, shaker plate and shaker.

FIG. 4A illustrates another view of a mounted manifold assembly 212 mounted on an incubator shelf 300. The shelf is carried on a pair of support legs 310 and 312 with attachment feet 314 and 316, respectively which are designed to mount in an incubator as shown in FIG. 5.

Figure 4B:
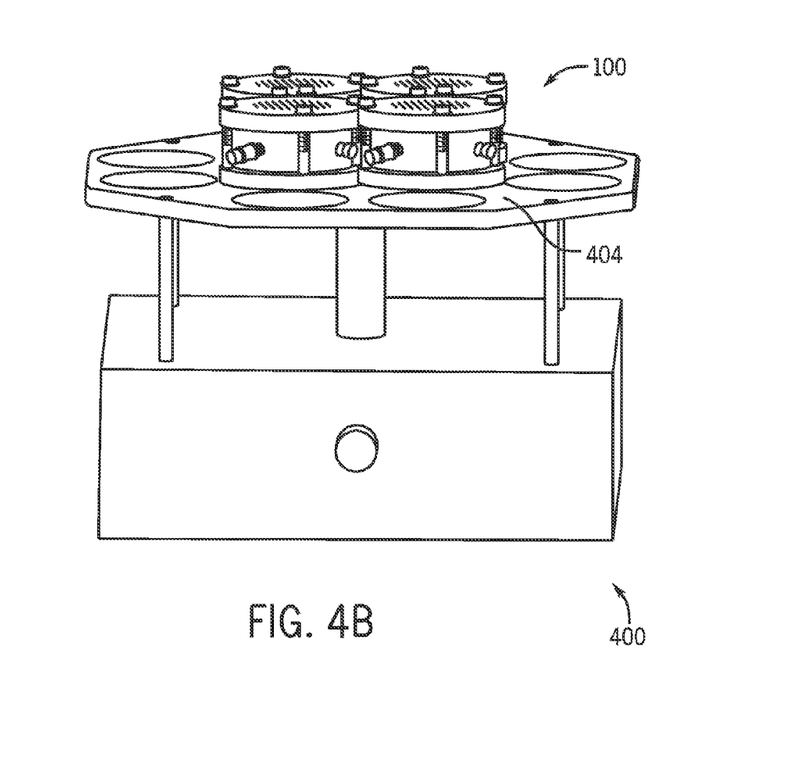

FIG. 4B shows a plurality of bioreactor chambers 100 mounted atop a Belly Dancer Shaker System 400 designed to be contained in an incubator. Additional openings are provided at 402 to accommodate additional chambers. The shaker system is one built by Stovall Life Science, Inc. of Greensboro, N.C. but equivalent systems may be used. The shaker provides a means of selectively cyclically agitating the cell culture media to enhance nutrient mass transport through the construct and gas transfer across the gas permeable membrane 114 (FIG. 2). The shaker system includes a shaker module 400 and a connected shaker plate 404 or platform on which are mounted the plurality of chambers 100.

It will be appreciated that the agitating movement of the bioreactor chamber creates varying motion in the nutrients containing fluid culture medium which may aid cell seeding on the substrate or help facilitate cell aggregation and adhesion as well as the transfer of nutrients within the substrate. The movement of the chamber may further generate varying multi-axial stresses in the tissue construct which provides added stimulation which may enhance tissue development, mechanical properties and function.

Figure 5:
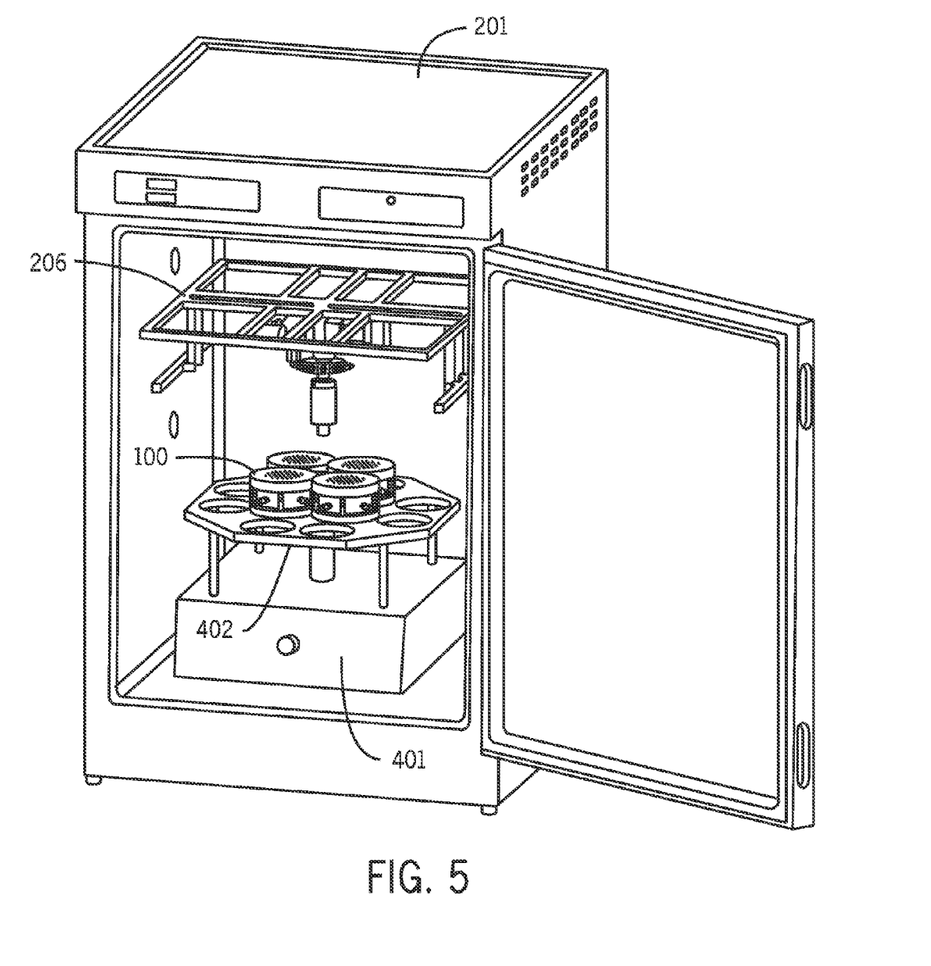
FIG. 5 depicts the assemblies of FIGS. 4A and 4B as assembled in an incubator.

FIG. 5 depicts the assemblies of FIGS. 4A and 4B as assembled in an incubator 202 where the actual tissue growth is carried on. Such incubators are available commercially and, of course, include their own temperature control systems to create the proper temperature environment for carrying on the tissue growth.

Figure 6:
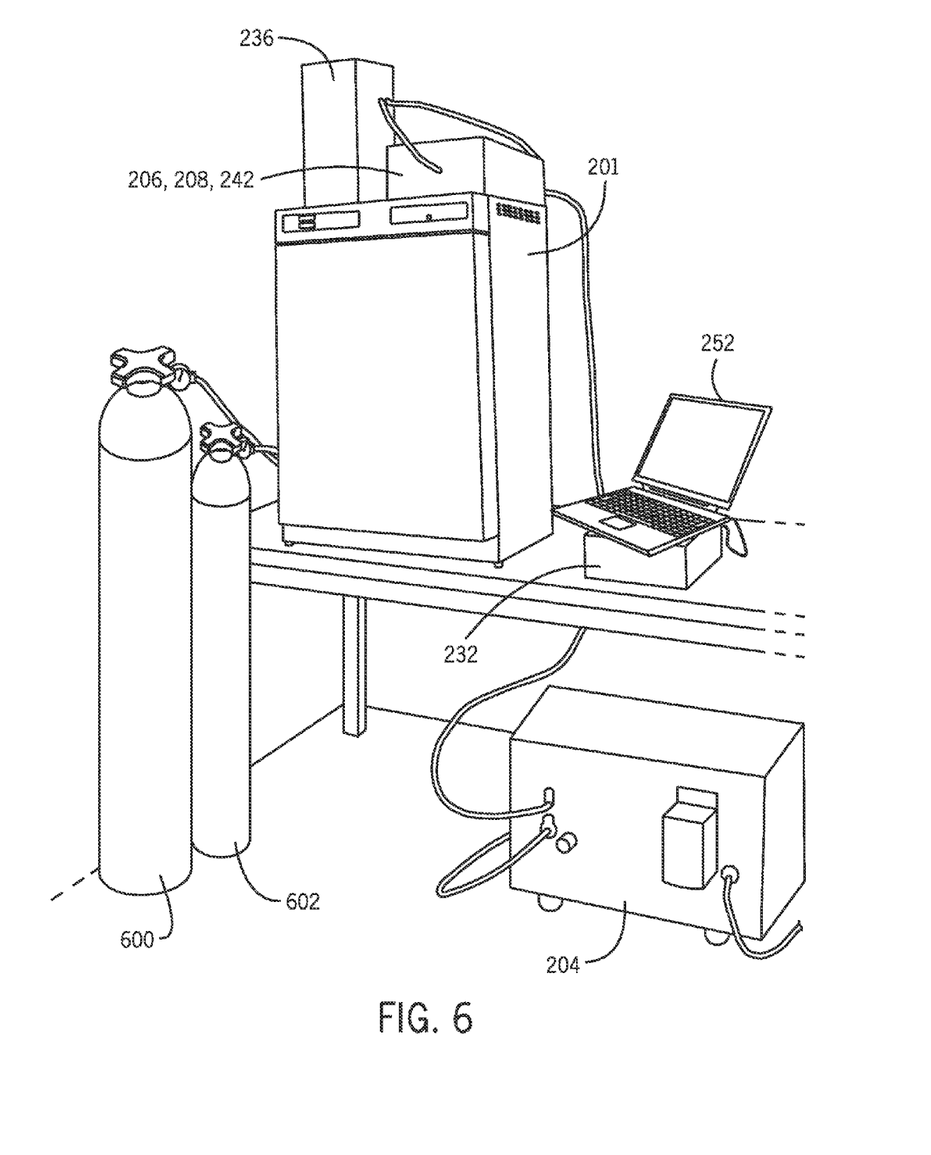
FIG. 6 depicts an entire system as it may be operated in a laboratory.

FIG. 6 depicts a typical view of an entire system, including all the auxiliary devices as would be typically set up in a tissue growth laboratory. Note that the pressurized air supply or pressure pack 204, together with heaters 208, 242, filter 206 and air drier 236 are situated outside the incubator 202, but are connected to the incubator through tubing connections as shown. Auxiliary gas tanks 600, 602 are also provided and are generally connected to the incubator gas inlet ports, but may be connected to media inlet ports of tissue growth chambers inside the incubator 202. Electrical control is supplied by controller 232 in combination with a personal computer. Both components may be programmed in any manner desired to control the tissue growth environmental conditions. Other embodiments may use alternative control platforms including but not limited to:

Programmable Logic Controllers, Personal Digital Assistants, mini computer, super computer, etc.

The embodiments provided herein are intended to demonstrate representative embodiments of the present subject matter. Variations in structure and design are possible without departing from the scope of the present invention, which is defined by the appended claims and their equivalents. Other embodiments for bioreactor configurations may include the combination of various elements and configurations as provided herein.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A bioreactor system for growing and conditioning constructs comprising:
   (a) a growth chamber for growing and conditioning at least one construct, said chamber being defined by a housing and providing at least one fluid culture media cavity, said fluid culture media cavity can act as a reservoir;
   (b) at least one source of dynamic pressurization and at least one rigid, pressurized space proximal to or contained within the chamber but separated from said fluid culture media cavity, said rigid, pressurized space pressurized by said source of dynamic pressurization to apply hydrostatic states of stress to developing tissues or cells of said construct, said housing having a passage between said rigid pressurized space and said fluid culture media cavity, said rigid pressurized space separated from said fluid culture media cavity by a deformable, non gas permeable membrane sealing an adjacent end of the culture media cavity and isolating the rigid pressurized space from the fluid culture media cavity;
   (c) at least one device for facilitating gas exchange within the chamber to maintain gas concentrations in the media cavity; and
   (d) a pressure control system coupled to said source of dynamic pressurization for delivering a constant or varying pressure profile to the rigid pressurized space, said pressure control system including a pressure transducer coupled to said fluid culture media cavity.

2. A bioreactor system as in claim 1 further comprising at least one gas permeable membrane to facilitate gas exchange between the at least one fluid culture media cavity and a desired gas environment.

3. A bioreactor system as in claim 1 further comprising at least one actuation device for applying agitation to said growth chamber to enhance convective mass transport within the chamber.

4. A bioreactor system as in claim 1 wherein said chamber comprises a chamber body and at least one endcap.

5. A bioreactor system as in claim 1, wherein said pressure control system is coupled to said source of dynamic pressurization that includes compressor and vacuum devices to enable control of pressure in a programmed manner.

6. A bioreactor system as in claim 5 wherein said pressure control system further comprises a multi-position valve, a distribution manifold and a relief valve, said multi-position valve connects said source of dynamic pressurization and said distribution manifold in a first position and connects said source of dynamic pressurization with said relief valve in a second position.

7. A bioreactor system as in claim 1 wherein said construct is housed in but not attached to said chamber.

8. A bioreactor system as in claim 3 wherein said construct is supported by, but not attached, to said chamber and wherein movement of said chamber by said at least one actuation device creates varying multi-axial stresses to said construct.

9. A bioreactor system as in claim 1 further comprising devices for sealing accesses to said chamber to facilitate enclosing, sterilizing, storing and shipping said growth chamber containing said construct.

10. A bioreactor system as in claim 1 wherein said construct comprises a biocompatible non-living three-dimensional framework having interstitial spaces bridgeable by cells.

11. A bioreactor system as in claim 1 wherein said construct is biological in nature and is comprised of one or more materials selected from the group consisting of extracellular matrix, decellularized tissue, native tissue explants, polymer matrices, woven fiber meshes, porous ceramic lattices, and porous metal structures.

12. A bioreactor system as in claim 1 wherein said chamber includes at least one access port for introducing nutrient-containing fluid culture media into said growth chamber.

13. A bioreactor system as in claim 1 substantially contained in an incubator.

14. A bioreactor system as in claim 1 comprising a plurality of growth chambers and a multi-fitting distribution/manifold separately connecting each said plurality of growth chambers with said source of dynamic pressurization.

15. A bioreactor system as in claim 8 wherein movement of said chamber further creates fluid flow around said construct.

16. A bioreactor system as in claim 2 wherein said non gas permeable membrane is not liquid permeable and wherein said gas permeable membrane is not liquid permeable.

17. A bioreactor system for growing and conditioning tissue, said system comprising:
   non-expandable growth chambers for growing and conditioning constructs, said chambers having non-expandable fluid culture media cavities;
   deformable, non gas permeable membranes that are positioned proximate the fluid culture media cavities but not within the fluid culture media cavities, said membranes block openings formed in said non-expandable growth chamber wherein said openings extend between an exterior of said growth chamber and an interior of said growth chamber;
   a source of dynamic pressurization coupled to an exterior of said chamber to apply hydrostatic states of stress to the constructs within said chambers, said hydrostatic states of stress resulting from applying pressurization to deform said deformable, non gas permeable membranes, said membranes separating said source of dynamic pressurization and said media cavities of said chambers between the exterior of said chamber and said fluid culture media cavities;
   a device for facilitating gas exchange within the chambers to maintain gas concentrations in the media cavities; and
   a pressure control system coupled to said source of dynamic pressurization for delivering at least one of constant and variable pressure, said pressure control system including a pressure transducer.

18. The bioreactor system as recited in claim 17, wherein said at least one of constant and variable pressure deforms said membranes coupled to said chambers.

19. The bioreactor system as recited in claim 17, wherein said chambers further include gas permeable membranes coupled to said chambers to facilitate gas exchange between the fluid culture media cavities and a gas source.

20. The bioreactor system as recited in claim 17, wherein said construct comprises a biocompatible, non-living, three-dimensional framework having spacing bridgeable by cells.

21. The bioreactor system as recited in claim 17, wherein said construct comprises a biological material selected from the group consisting of tissue, extracellular matrix, decellularized tissue, native tissue explants, polymer matrices, woven fiber meshes, porous ceramic lattices, and porous metal structures.

22. A bioreactor system for growing and conditioning constructs comprising:
   a chamber for growing and conditioning a construct therein, said chamber including a housing having non-expandable sidewalls and first and second enclosed ends, wherein an interior of the non-expandable sidewalls defines a non-expandable media cavity;
   said first enclosed end of said housing including a pressure port having a pressure gas space formed in said first enclosed end and wherein said pressure port is suitable for connection to a pressure delivery system;
   said second enclosed end of said housing including an exchange port in fluid communication with said non-expandable media cavity of said chamber;
   a first deformable membrane that covers and seals a first end of said media cavity and that isolates said non-expandable media cavity from said pressure port wherein said pressure gas space is pressurizeable by the pressure delivery system; and
   a second membrane that covers and seals a second end of said media cavity and that is positioned between said media cavity and said exchange port.

23. A bioreactor system as recited in claim 22, further including a media port coupled to said chamber and in fluid communication with said media cavity.

24. A bioreactor system as recited in claim 22, further including a pressure control system coupled to said pressure delivery system for delivering a constant or varying pressure profile.

25. A bioreactor system as recited in claim 22, wherein said first membrane is of a non gas-permeable construction.

26. A bioreactor system as recited in claim 22, wherein said second membrane is of a non gas-permeable construction.

27. A bioreactor system as recited in claim 22, wherein said first membrane is of a gas permeable construction.

28. A bioreactor system as recited in claim 22, wherein said second membrane is of a gas permeable construction.

29. A bioreactor system as recited in claim 22, further comprising at least one actuation device for applying agitation to said chamber.

30. A bioreactor system as recited in claim 22, wherein pressurizing said pressure gas space creates a hydrostatic state of stress to the construct within the chamber.

31. A bioreactor system as recited in claim 22, wherein movement of said chamber assists fluid flow around the construct.

* * * * *